United States Patent [19]
Byatt et al.

[11] Patent Number: 5,982,498
[45] Date of Patent: Nov. 9, 1999

[54] METHOD FOR DETERMINING THE STRUCTURE OF A BODY SURFACE

[75] Inventors: Anthony Byatt, Klingnau; Thomas Kleiner, Nussbaumen; Daniel Matter, Brugg, all of Switzerland

[73] Assignee: ABB Research Ltd., Zurich, Switzerland

[21] Appl. No.: 09/094,694

[22] Filed: Jun. 15, 1998

[30] Foreign Application Priority Data

Jun. 16, 1997 [DE] Germany ............................ 197 25 337

[51] Int. Cl.$^6$ .......................... G01N 21/84; G01N 21/00; G01J 1/42; G01B 11/30
[52] U.S. Cl. .......................... 356/429; 356/121; 356/237; 356/218; 356/371; 356/138
[58] Field of Search .................................... 356/121, 429, 356/237, 218, 138, 371

[56] References Cited

U.S. PATENT DOCUMENTS 3,922,093  11/1975  Dandliker et al. ........................ 356/120
5,394,247  2/1995  Vahey et al. .............................. 356/429

FOREIGN PATENT DOCUMENTS

312704A1   6/1983  Germany .
3413558A1  10/1985  Germany .

*Primary Examiner*—Frank G. Font
*Assistant Examiner*—Roy M. Punnoose
*Attorney, Agent, or Firm*—Burns, Doane, Swecker & Mathis, L.L.P.

[57] ABSTRACT

A moving body surface or paper web (1) to be investigated is irradiated at at least one irradiation site by 3 laser light sources of a surface structure measuring device (FOS1, FOS2). Reflected and scattered light is detected and evaluated in order to calculate ellipse points. An ellipse major axis ratio corresponding to a fiber orientation ratio, and a fiber orientation angle are calculated from the ellipse parameters thus obtained. Identical measurements and calculations are carried out periodically on an isotropic sample (NO) and a sample (Nx) having a fiber orientation similar to that of the body surface to be measured, in order to calibrate the measurements at the body surface (1).

13 Claims, 4 Drawing Sheets

METHOD FOR DETERMINING THE STRUCTURE OF A BODY SURFACE

This application claims priority under 35 U.S.C. §§119 and/or to No. 197 25 337.7 filed in Germany on Jun. 16, 1997; the entire content of which is hereby incorporated by reference.

BACKGROUND OF THE INVENTION

1. Field of the Invention

The invention relates to a method for determining the structure of a body surface.

2. Discussion of background

The invention according to the independent patent claim 1 refers to a prior art as is disclosed in DE 34 13 558 A1. Specified there is a method for contactless determination of the fiber orientation in paper on running paper webs, in which laser light is irradiated into the paper in radiation pulses and the light intensity in the region adjacent to the irradiation site on the irradiation side or on the transmission side at a plurality of prescribed measuring points distributed over an angle of 180° around the irradiation site is measured by 2 detector pairs at a predetermined distance from the irradiation site, and the electric measured values obtained are compared with one another. The irradiation site has a diameter of <100 µm. Extraneous radiation is suppressed by stops or masks. Elliptical curves or intensity distributions of the detected light are yielded as a function of the average value of the fiber orientation by rotating the detector pairs about the irradiation site. No calibration of the measurement results is provided.

A method for optically determining the surface structure of workpieces is presented in DE 31 27 604 A1. For this purpose, the light reflected from a body surface is detected at an azimuth angle and at a multiplicity of lateral angles by using a rotatably mounted light-deflecting prism and stationary detectors to measure the scattered-light or reflected-light distribution.

SUMMARY OF THE INVENTION

Accordingly, one object of the invention, as defined in patent claim 1, is to provide a novel solution to further developing a method for determining the structure of a body surface of the type mentioned at the beginning in such a way that the surface structure can be determined at arbitrary points on a moving material surface.

Advantageous refinements of the invention are defined in the dependent patent claims.

One advantage of the invention consists in that roughness anisotropy values of the surface to be investigated can be determined quickly and simply.

In accordance with an advantageous refinement of the invention, the roughness anisotropy values determined can be checked in a quasi-continuous fashion using standards.

The method according to the invention is particularly suitable for determining the fiber orientation in papers, which is of interest, inter alia, for their tearing strength and printability. Irradiated light is reflected and scattered differently depending on the nature of the surface of said paper. Measurement is made of surface roughness anisotropy, which is directly related to the fiber orientation distribution.

If light impinges on the paper surface at a shallow angle, a large portion thereof is reflected, a portion is absorbed in the paper, a portion is scattered diffusely from the paper, and a small portion is transmitted. In the case of the method according to the invention, light reflected and scattered at the body surface is detected and evaluated.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
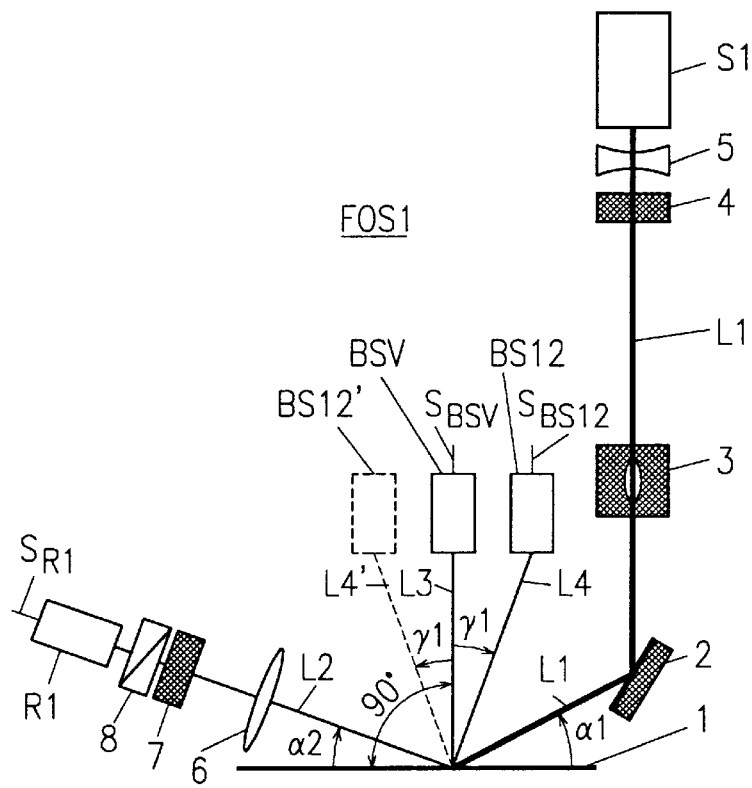
FIG. 1 shows a representation of the principle of a surface-structure measuring device in a representation of a vertical section.
Figure 3:
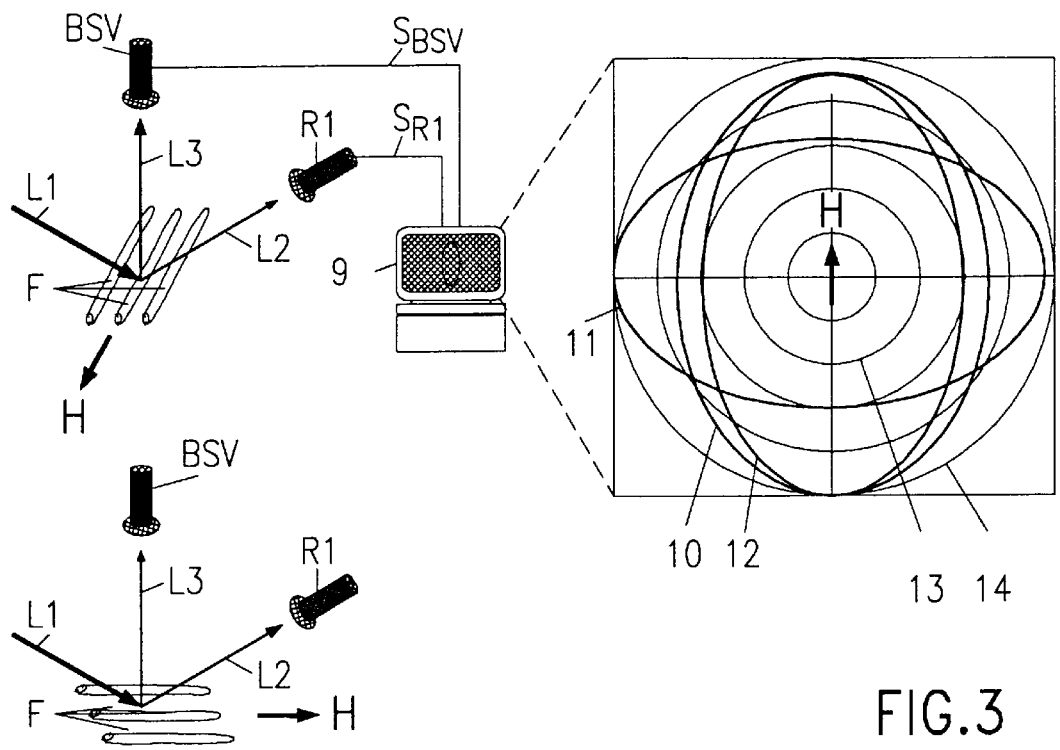
FIG. 3 shows a representation of the principle of a roughness anisotropy measurement on paper surfaces.

Referring now to the drawings, wherein like reference numerals designate identical or corresponding parts throughout the several views, FIG. 1 shows a diagram of a surface-structure measuring device (FOS1) for measuring the roughness anisotropy at a body surface or paper web (1) in accordance with FIG. 3. From a HeNe laser with an electric power of 1 mW, or from a light source (S1), linearly polarized laser light or incident light (L1) whose plane of polarization is oriented parallel to the surface of the paper web (1) and perpendicular to a plane of incidence of the incident light (L1) is directed onto the paper web (1) at an incidence angle ($\alpha$1) in the angular range of 10°–30°, preferably of 20° via a concave lens (5), a gray filter or attenuator (4) with a light attenuation factor of 20%, an elliptical light stop (3) and a mirror or reflector (2). From there, a portion of the incident light (L1) is reflected as reflected light (L2) at an azimuthal angle of reflection ($\alpha$2) which is at least approximately equal to the incidence angle ($\alpha$1) via a convex lens (6), a gray filter or attenuator (7) and an analyzer (8) to a reflected-light detector (R1) which supplies on the output side an electric light power signal ($S_{R1}$) which is proportional to the received light power. Another portion of the incident light (L1) is reflected at the surface of the paper web (1) from fibers (F), compare FIG. 3, as orthogonal reflected light (L3) at an angle of 90° to the plane of the paper web (1) via a lens (not represented) and an analyzer (not represented) to an orthogonal light detector (BSV) which supplies on the output side an electric light power signal ($S_{BSV}$) which is proportional to the received light power. A further portion of the incident light (L1) is backscattered by the surface of the paper web (1) as backscattered light (L4) at a scattered-light angle or backscatter angle (γ1) in the angular region of 10°–30°, preferably of 25°, to the orthogonal with respect to the paper web (1) via a lens (not represented) and an analyzer (not represented) to a backscattered-light detector (BS12) which supplies on the output side an electric light power signal ($S_{BS12}$) which is proportional to the received light power. Instead of the backscatteredlight detector (BS12), it is also possible to use a scattered-light detector (BS12') in the forward direction of a scattered-light beam (L4'), as indicated by dashes in FIG. 1. The scattering angle (−β1) has the opposite sign in this case.

Figure 1A:
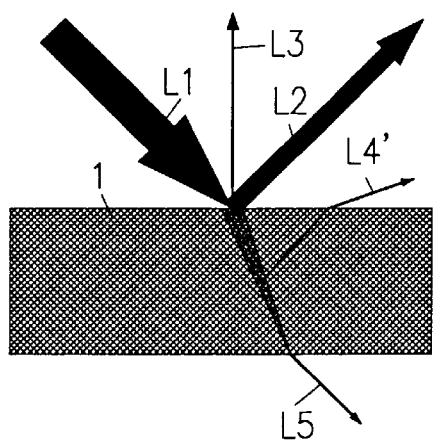
FIG. 1a shows the interaction of light with a paper surface.

FIG. 1a illustrates the interaction of incident light (L1) on the paper web (1). A portion of the incident light (L1) is reflected at the azimuthal angle of reflection (α2), light (L2), a portion is reflected orthogonally, reflected light (L3), a portion is absorbed in the paper web (1), a portion is scattered from the paper (1), light (L4') and a portion is passed as transmitted light (L5).

Figure 2:
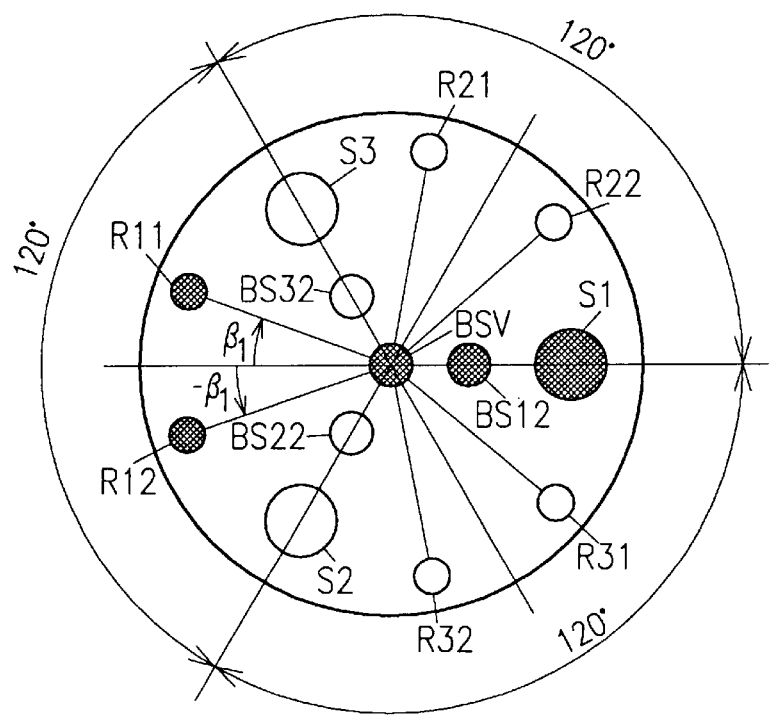
FIG. 2 shows a representation of the principle of a surface-structure measuring device in plan view.

Instead of only one reflected-light detector (R1) in the plane of incidence of the incident light (L1), as represented in FIG. 1, the surface-structure measuring device (FOS1) can have 2 reflected-light detectors (R11) and (R12) which are arranged at the azimuthal angle of reflection (α2) with respect to the plane of the paper web (1) and, in addition, at a lateral angle of reflection (β1) or (−β1) with respect to the plane of incidence of the incident light (L1) compare FIG. 2. FIG. 2 shows, in a diagrammatic plan view 3, similar surface-structure measuring devices, which are arranged in the horizontal plane (plane of the paper web (1)) mutually offset by 120°. The other two light sources are denoted correspondingly by (S2) and (S3), the reflected-light detectors by (R21), (R22) and (R31), (R32), respectively, and the backscattered-light detectors by (BS21), (BS22) and (BS31), (BS32), respectively. The orthogonal-light detector (BSV) is common to all 3 surface-structure measuring devices.

FIG. 3 shows a representation of the principle of a roughness anisotropy measurement on paper surfaces, having a surface-structure measuring device (FOS1) in accordance with FIGS. 1 and 2, but without the use of the scattered-light detectors (BS12), (BS12'). The light power signals ($S_{BSV}$) and ($S_{R1}$) are fed to a computer with a display device (9), which displays or supplies elliptical curves 10–12 as a function of said signals. In this process, the paper web (1) is rotated by 360° about the point where the incident light (L1) impinges on it and measured at angular spacings of 7.5°. (H) denotes the principal direction of the fibers (F) in the paper web (1). If the principal direction (H) of the fibers (F) is in the plane of the incident light (L1), the predominant portion of the incident light (L1) is reflected at the azimuthal angle of reflection (α2), compare FIG. 3, bottom left; if, by contrast, the principal fiber direction (H) is orientated perpendicular to the plane of incidence, the portion of the orthogonal reflected light (L3) is larger than that of the light (L2) reflected at the azimuthal angle of reflection (α2), compare FIG. 3, top left. The elliptical curve (10) in the right-hand part of FIG. 3 shows a 360° light intensity curve, measured using a reflected-light detector (R1) for an azimuthal angle of reflection (α2) of 20°, in accordance with FIG. 1, with a lateral angle of reflection β1=0°. The elliptical curve (11) displays a 360° light intensity curve for orthogonal reflected light (L3), measured using the orthogonallight detector (BSV) at 90° to the plane of the paper web (1). The elliptical curve (12) is yielded from the ratio of the measured values of curve (10) to those of curve (11). Circles denoted by (13) and (14) correspond to light-intensity values of 50% and 100%, respectively.

Figure 4:
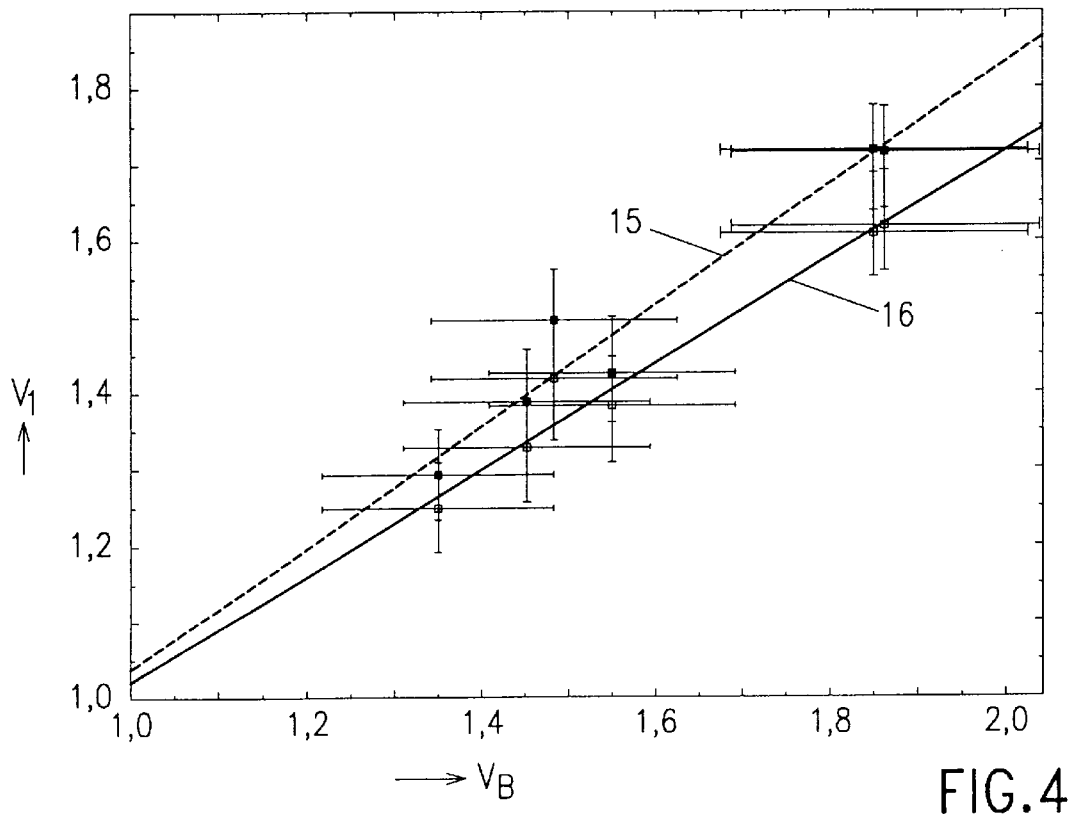
FIG. 4 shows a representation of the correlation between experimentally determined values and values obtained by an image-processing method for the fiber orientation in paper.

FIG. 4 shows a representation of the correlation between experimentally determined values and so-called IPST standard values of the fiber orientation in paper having a weight per unit area of approximately 80 g/m² corresponding to photocopier paper. A ratio ($V_1$) of measured values of the ellipse semimajor axis to the ellipse semiminor axis is given on the ordinate, and the ratio ($V_B$) of fiber orientation ratios, which were determined using a conventional image-processing method, of the ellipse semimajor axis to the ellipse semiminor axis is given on the abscissa. The measurements were carried out with 3 paper samples, the front and rear sides being measured separately. Averaging was carried out over 3 measurements in each case. The error bars drawn in show the standard deviation of the averaged measured values and an error estimate of 10% for the IPST standard values. A straight line denoted by (16) represents a linear approximation of light intensity conditions which was obtained using a reflected-light detector (R1) in the plane of the incident light (L1) (β1=0°). A straight line denoted by (15) represents a linear approximation of light intensity conditions which was obtained using a reflected-light detector (R11) about a lateral angle of reflection (β1) of 20° outside the plane of the incident light (L1). It may be seen from this that the two straight lines (15) and (16) differ only in their gradient, and can therefore be converted simply into one another. A steeper gradient of the straight line (15) effects a higher measurement sensitivity, and so it is normal to choose β1>1.

Figure 5:
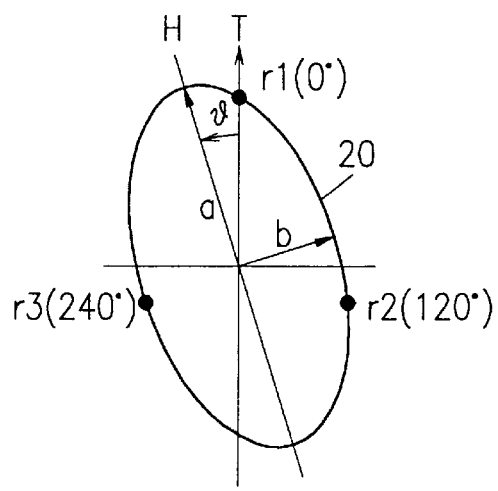
FIG. 5 shows an elliptic curve formed from 3 ellipse points calculated from measured values, for the purpose of explaining the determination of the fiber orientation ratio and the fiber orientation angle.

The calculation of the fiber orientation ratio or major axis ratio v=a/b of an ellipse (20), the shape of which can be defined by 3 calculated ellipse points r1, r2, r3, as well as of a fiber orientation angle φ, which denotes the inclination of the major axis of the ellipse (20) with respect to the principal fiber direction (H) or the ellipse point (r1), is explained below with the aid of FIG. 5. Here, a denotes the absolute value of the ellipse semimajor axis, and b that of the ellipse semiminor axis. The 3 ellipse points (r1, r2, r3) are calculated as follows:

$$ri = S_{Ri1} \cdot S_{Ri2}/(S_{BSi2} \cdot S_{BSV})$$

where i=1, 2, 3, corresponding to 0°, 120° and 240°, for the 3 surface-structure measuring devices in accordance with FIG. 2. The fiber orientation angle φ can thus be calculated in accordance with:

$$\phi = 0.5 \cdot \arctan[(3^{0.5}(r2-r3)/(r2+r3-2 \cdot r1)]$$

The ellipse major axis ratio V can be calculated in accordance with:

$$V = a/b = (k+1)/(k-1), \text{ where}$$

$$k = (r1+r2+r3)/[(r2+r3-2 \cdot r1)^{0.5} + 3 \cdot (r2-r3)^{0.5}]$$

The indices 1 or x or B for the variables θ and V relate to the body surface (1) or to a sample (Nx) having a fiber orientation similar to that of the body surface to be measured, or to the image-processing standard values which are known in advance on the basis of evaluations of enlarged photographs of (Nx).

For this surface-structure measuring device (FOS1), there is a total of 3 light sources (S1, S2, S3) and 10 light detectors whose output signals are evaluated.

Figure 6:
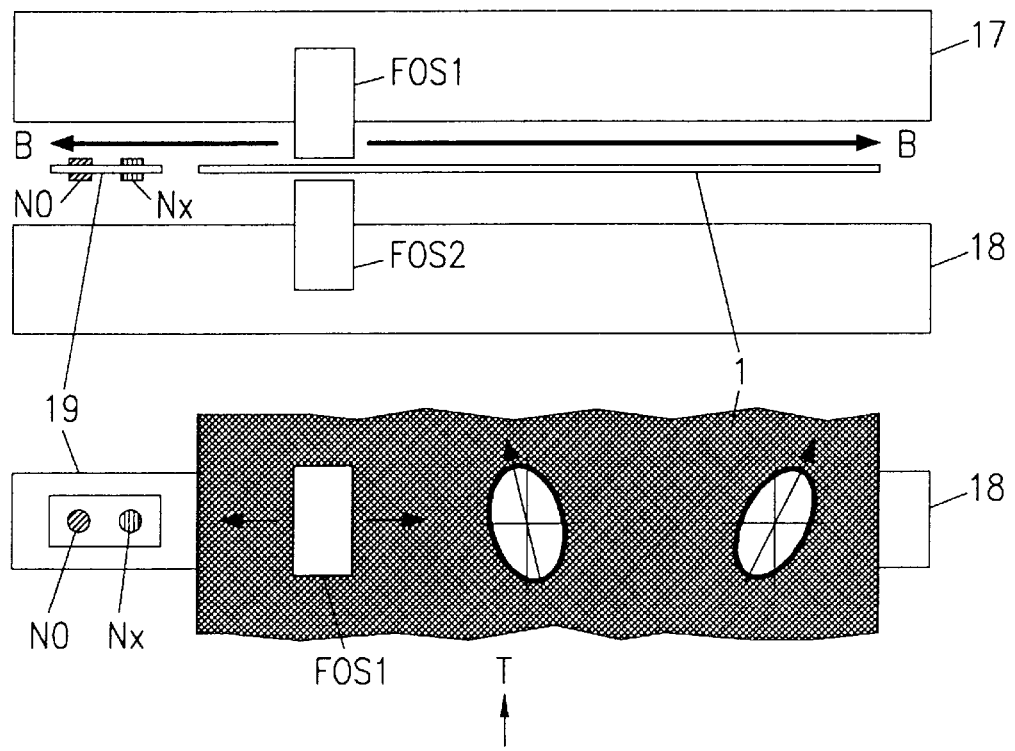
FIG. 6 shows a representation of the principle of a device for calibrating the fiber orientation by means of a fiber orientation standard and an ideal diffuse surface.
Figure 7:
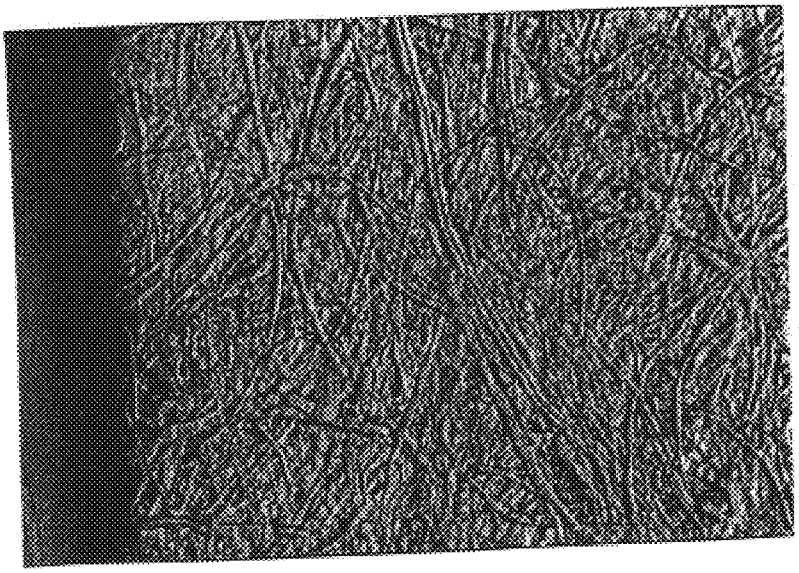
FIG. 7 and 8 show examples of fiber orientation standards.
Figure 8:
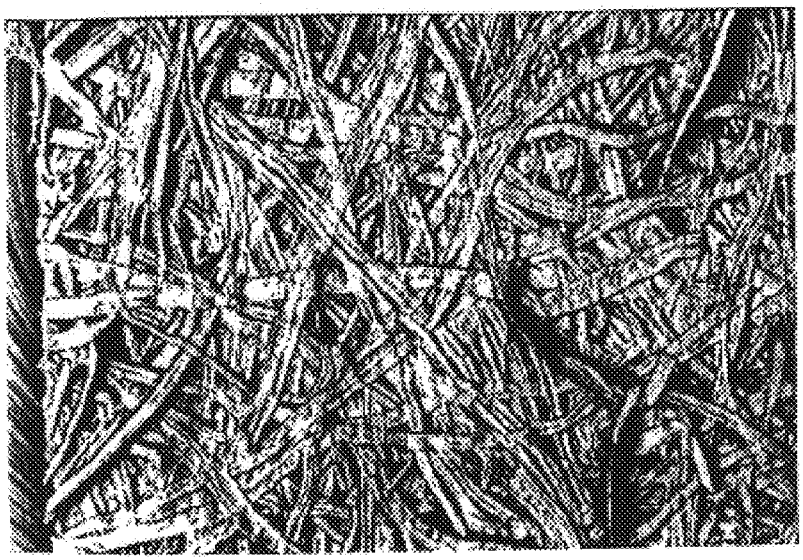
Figure 9:
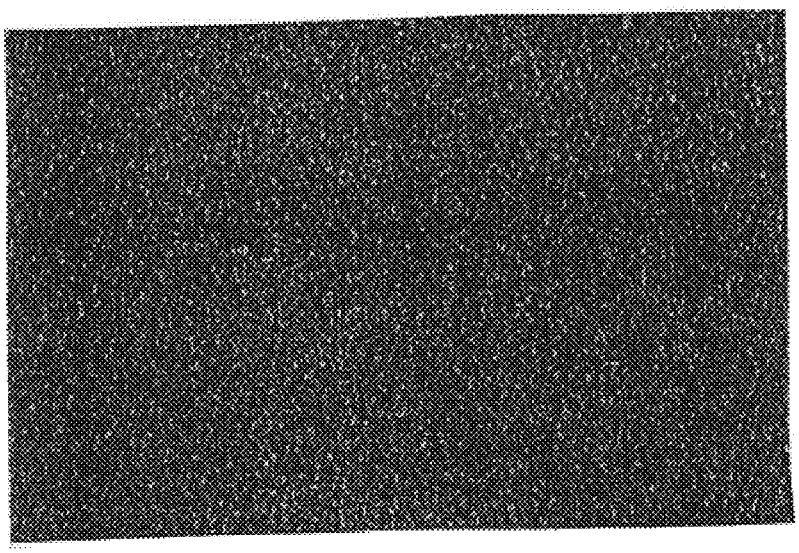
FIG. 9 shows an example of an ideal diffuse surface for use in the device for calibrating in accordance with FIG. 5.

The upper part of FIG. 6 shows in cross section a representation of the principle of a device for calibrating the fiber orientation by means of a fiber-orientation standard, that is to say a sample (Nx) having a fiber orientation similar to that of the body surface to be measured, compare FIGS. 7 and 8, and an ideally diffuse surface of an isotropic sample (N0), compare FIG. 9, which two samples are arranged in the plane of the paper web (1) on a sample carrier (19) between an upper and lower measuring platform (17) and (18), respectively. Arranged respectively above the paper web (1) and below the latter are a surface-structure measuring device (FOS1) or (FOS2), and they can be displaced parallel to the plane of the paper web (1) and at right angles to the transport direction (T) thereof in directions (B—B). The transport direction (T) of the paper web (1) is generally also the principal fiber direction (H) thereof. As is indicated in the lower part of FIG. 6, the principal fiber direction (H) to be measured can differ over the width of the paper web (1). Said figure represents a plan view of the paper web (1).

FIGS. 7 and 8 represent electron microscope photographs with a 60-fold enlargement of photocopier paper and cardboard, which are used as a sample (Nx) having a fiber orientation similar to that of the body surface to be measured. Similar exchangeable standards exist for all body surfaces which come into consideration for comparison, for example of newsprint, polyamide paper, polyamide/polyester etc. Standards of polyamide and polyamide/polyester are also suitable for calibrating Xerox paper, cardboard, etc., since they remain unchanged in the moist and warm environment of a paper-making machine (not represented).

An ellipse major axis ratio $V_B$ and a fiber orientation angle $\theta_B$ are determined from each of these standard surfaces using image-processing methods, which are generally known and therefore not described here, for example $V_B=1.6$ and $\theta_B=6°$. Then, by means of the surface-structure measuring device (FOS1), for example, the variables $V_x$ and $\theta_x$ are determined by moving the surface-structure measuring device (FOS1) over the sample (Nx) in a measuring fashion. The ratio $V_B/V_x$ is now formed as a calibration factor by which all the $V_1$ values determined on the paper web (1) are then multiplied. Furthermore, a calibration angle $\Delta=\theta_B-\theta_x$ is formed by the sample (Nx) and added to the $\theta_1$ values, which have been determined on the paper web (1).

FIG. 9 shows an electron microscope photograph with 60-fold enlargement of a fine ceramic which is used as an isotropic sample (N0) for zero-point determination of the measurements, that is to say the intensities of the laser diodes of the light detectors are standardized in such a way that an ellipse major axis ratio $V_1=1$ results for all the light sources (S1–S3). It would also be possible to use an isotropic rough ceramic sample.

It is important that the surface-structure measuring devices (FOS1) and, if appropriate (FOS2) pass over the samples (N0) and (Nx) in periodic time intervals and that new scaled values $V_B/V_x$ and $\Delta=\theta_B-\theta_x$ are formed in the process.

The light sources (S1–S3) can be driven sequentially at different frequencies of, for example, 10 kHz, 20 kHz and 40 kHz, or all at only one frequency of, for example, 40 kHz. Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method for determining the structure of a body surface (1), it being the case that
   a) at least one irradiation site of the body surface (1) is irradiated at the irradiation site by an incident light beam (L1) at a prescribable incidence angle ($\alpha 1$) to the plane of the body surface (1),
   b) the irradiation site is irradiated with an incident light beam (L1) from at least 3 lateral angles (0°, 120°, 240°),
   c) for each incident light beam (L1) at least one light beam (L2) reflected at an azimuthal angle of reflection ($\alpha 2$) is detected, and a light power signal ($S_{R1}$) proportional thereto is derived,
   d) a reflected light beam (L3) orthogonal to the plane of the body surface (1) is detected from the irradiation site, and a light power signal ($S_{BSV}$) proportional thereto is derived,
   e) ellipse points (r1, r2, r3) are calculated as a function of said light power signals ($S_{R1}$, $S_{BSV}$)
   f) an ellipse major axis ratio $V_1=a/b$, a=ellipse semimajor axis, b=ellipse semiminor axis and
   g) a fiber orientation angle ($\theta_1$) calculated from said points, and
   h) at least this major axis ratio $V_1$ is compared with a standard major axis ratio $V_B$ which is derived from a sample (Nx) having a fiber orientation similar to that of the body surface (1) to be measured.

2. The method as claimed in claim 1, wherein the ellipse major axis ratio $V_1$ is multiplied by a factor of $V_B/V_X$, where $V_B$=main axis ratio for a prescribed standard value of a sample (Nx) having a fiber orientation similar to that of the body surface to be measured, and $V_x$ ellipse major axis ratio for the sample (Nx), measured instead of the body surface (1).

3. The method as claimed in claim 1, wherein a calibration angle of $\Delta=\theta_B-\theta_x$ is added to the fiber orientation angle $\theta_1$ of the body surface (1), where $\theta_B$=prescribed standard fiber orientation angle for the sample (Nx) having a fiber orientation similar to that of the body surface (1) to be measured, and $\theta_x$=fiber orientation angle for the sample (Nx) measured instead of the body surface (1).

4. The method as claimed in claim 1,
   a) wherein a radiation beam (L4, L4') emerging from the body surface (1), in particular paper, is detected at a prescribable distance from the irradiation site on the irradiation side in the region adjacent to the irradiation site and is evaluated, and
   b) wherein the ellipse points (r1, r2, r3) are calculated in accordance with:

$$ri = S_{Ri1} \cdot S_{Ri2}/(S_{BSi2} \cdot S_{BSV})$$

where i=1, 2, 3, in accordance with 0°, 120°, 240°, $S_{Ri1}$, $S_{Ri2}$=light power signals detected by reflected light (L2) at a prescribable azimuthal angle of reflection ($\alpha 2$),
   $S_{BSi2}$=light power signal detected by scattered light (L4, L4') at a prescribable scattering angle ($\gamma 1$, $-\gamma 1$),
   and $S_{BSV}$=light power signal from the orthogonal reflected light beam (L3) of the irradiation site.

5. The method as claimed in claim 4, wherein the light power signals ($S_{B11}$, $S_{B12}$) detected at an azimuthal angle of reflection ($\alpha 2$) have a prescribable lateral angle of reflection ($\beta 1$) in the angular region of 5°–30° with respect to a light incidence plane of the incidence light beam (L1).

6. The method as claimed in claim 1,
   a) wherein only one light power signal $S_{R1}$ is detected at an azimuthal angle of reflection ($\alpha 2$) and,
   b) wherein the ellipse point (r1, r2, r3) are calculated in accordance with:

$$ri = S_{Ri}/(S_{BSi2} \cdot S_{BSV})$$

where i=1, 2, 3, corresponding to 0°, 120°, 240°, $S_{BSi2}$= light power signal detected by scattered light (L4, L4') at a prescribable scattering angle (γ1, −γ1), and $S_{BSV}$=light power signal from an orthogonal reflected light beam (L3) of the irradiation site.

7. The method as claimed in claim 1, wherein the incidence angle (α1) is in the angular region of 10°–30°.

8. The method as claimed in claim 4, wherein the fiber orientation angle θ is calculated in accordance with:

$$\theta = 0.5 \cdot \arctan[(3^{0.5}(r2+r3)/(r2-r3-2 \cdot r1)]$$

9. The method as claimed in claim 4, wherein the ellipse main axis ratio $V_1$ is calculated in accordance with:

$$V_1 = (k+1)/(k-1,$$

where:

$$k = (r1+r2+r3)/[(r2+r3-2 \cdot r1)^{0.5} + 3 \cdot (r2-r3)^{0.5}]$$

10. The method as claimed in claim 1,
  a) wherein the method is carried out on at least one surface of a moving paper web (1), and
  b) wherein at prescribable time intervals at least one sample (Nx) having a fiber orientation similar to that of the body surface to be measured is measured and evaluated for the purpose of calibrating the measured values derived from the paper web (1).

11. The method of claim 6, wherein the ellipse points (r1, r2, r3) are calculated in accordance with:

$$ri = S_{Ri}/S_{BSV}.$$

12. The method of claim 7, wherein the incident light beam is linearly polarized parallel to the body surface.

13. The method of claim 10, wherein the incident light beam (L1) of all the light sources (S1–S3) is directed at prescribable time intervals onto an isotropic sample (N0) and light power signals ($S_{R1}$, $S_{BSV}$) derived therefrom are calibrated in such a way that an ellipse major axis ratio of $V_1=1$ results for all the light sources (S1–S3).

\* \* \* \* \*